United States Patent [19]

de Toledo

[11] Patent Number: 5,065,769
[45] Date of Patent: Nov. 19, 1991

[54] SMALL DIAMETER GUIDEWIRES OF MULTI-FILAR, CROSS-WOUND COILS

[75] Inventor: Fernando A. de Toledo, Concord, Mass.

[73] Assignee: Boston Scientific Corporation, Watertown, Mass.

[21] Appl. No.: 642,543

[22] Filed: Jan. 18, 1991

Related U.S. Application Data

[63] Continuation of Ser. No. 276,106, Nov. 23, 1988, abandoned, which is a continuation-in-part of Ser. No. 170,514, Mar. 21, 1988, Pat. No. 4,932,419.

[51] Int. Cl.⁵ .......................................... A61M 25/00
[52] U.S. Cl. .................................. 128/772; 128/657; 604/282
[58] Field of Search .................... 604/95, 170, 282; 128/657, 772

[56] References Cited

U.S. PATENT DOCUMENTS

| | | |
|---|---|---|
| 623,022 | 4/1899 | Johnson . |
| 707,775 | 8/1902 | Harris . |
| 2,118,631 | 5/1938 | Wappler .................. 128/349 |
| 2,560,915 | 7/1951 | Bamberger ............... 128/350 |
| 3,467,101 | 9/1969 | Fogarty et al. ........... 128/348 |
| 3,550,384 | 1/1971 | Pierie et al. .............. 128/657 |
| 3,749,085 | 5/1977 | Willson et al. ........... 128/772 |
| 3,749,086 | 7/1973 | Kline et al. ............... 128/2 M |
| 3,757,768 | 9/1973 | Kline et al. ............... 128/2 M |
| 3,773,034 | 11/1973 | Burns et al. .............. 128/2 M |
| 3,841,308 | 10/1974 | Tate ......................... 128/2 M |
| 3,973,556 | 8/1976 | Fleischhacker et al. .... 128/2 M |
| 4,020,829 | 5/1977 | Willson et al. ........... 128/2 M |
| 4,052,989 | 10/1977 | Kline ....................... 128/349 R |
| 4,068,660 | 1/1978 | Beck ........................ 128/214.4 |
| 4,173,981 | 11/1979 | Mortensen ............... 128/348 |
| 4,222,380 | 9/1980 | Terayama ................ 128/216 |
| 4,307,722 | 12/1981 | Evans ...................... 128/344 |
| 4,318,402 | 3/1982 | Vaillancourt ............ 128/214.4 |
| 4,351,341 | 9/1982 | Goldberg et al. ........ 128/348 |
| 4,368,730 | 1/1983 | Sharrock ................. 604/158 |
| 4,444,188 | 4/1984 | Bazell et al. ............. 128/348.1 |
| 4,493,696 | 1/1985 | Uldall ...................... 604/43 |
| 4,534,363 | 8/1975 | Gold ........................ 128/772 |
| 4,548,206 | 10/1985 | Osborne .................. 128/772 |
| 4,561,439 | 12/1985 | Bishop et al. ........... 128/348.1 |
| 4,579,127 | 4/1986 | Haacke .................... 128/772 |
| 4,642,092 | 2/1987 | Moss ....................... 604/43 |
| 4,676,249 | 6/1987 | Arenas et al. ........... 128/657 |
| 4,692,153 | 8/1987 | Berlin et al. ............. 604/171 |
| 4,715,378 | 12/1987 | Pope, Jr. et al. ......... 128/344 |
| 4,719,924 | 1/1988 | Crittenden et al. ...... 128/772 |
| 4,721,117 | 1/1988 | Mar et al. ................ 128/772 |
| 4,779,628 | 10/1988 | Mackek ................... 128/772 |
| 4,798,598 | 1/1989 | Bonello et al. .......... 128/772 X |
| 4,800,890 | 1/1989 | Cramer .................... 128/657 |
| 4,846,186 | 7/1989 | Box et al. ................ 604/164 X |

FOREIGN PATENT DOCUMENTS

WO88/00810 8/1981 World Int. Prop. O. .
WO88/00844 2/1988 World Int. Prop. O. .

OTHER PUBLICATIONS

USCI "Open Ended Guidewire", (Est. 1984).
Patent Cooperation Treaty International Search Report, PCT/US89/05098, 23 Nov. 1988.

*Primary Examiner*—C. Fred Rosenbaum
*Assistant Examiner*—Corrine Maglione
*Attorney, Agent, or Firm*—Fish & Richardson

[57] ABSTRACT

A medical guidewire having a distal tip portion for advancement through a body by application of force to a proximal end portion, comprising: an elongated multi-filar coil structural element, and disposed thereabout and along a substantial portion of the length of the structural element, a sheath formed of material that is non-corrosive within the body, the sheath being adapted to flex in unison with the structural element without kinking, the sheath and structural element in combination having a torque response along the joined length approaching 1:1, thereby allowing control of the distal tip at the guidewire within a body by application of rotational force to the proximal end portion outside the body.

20 Claims, 2 Drawing Sheets

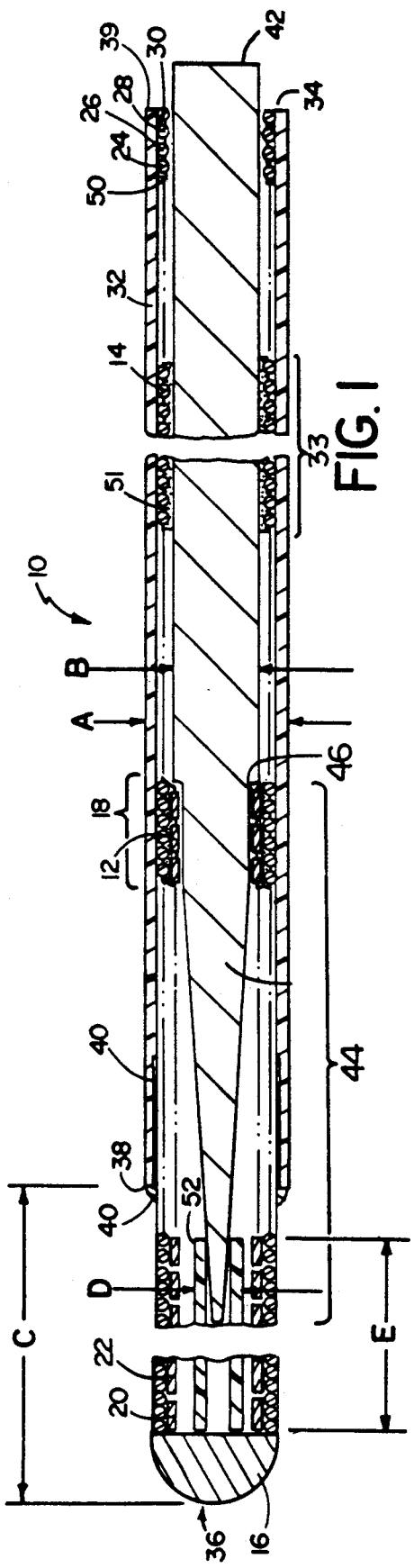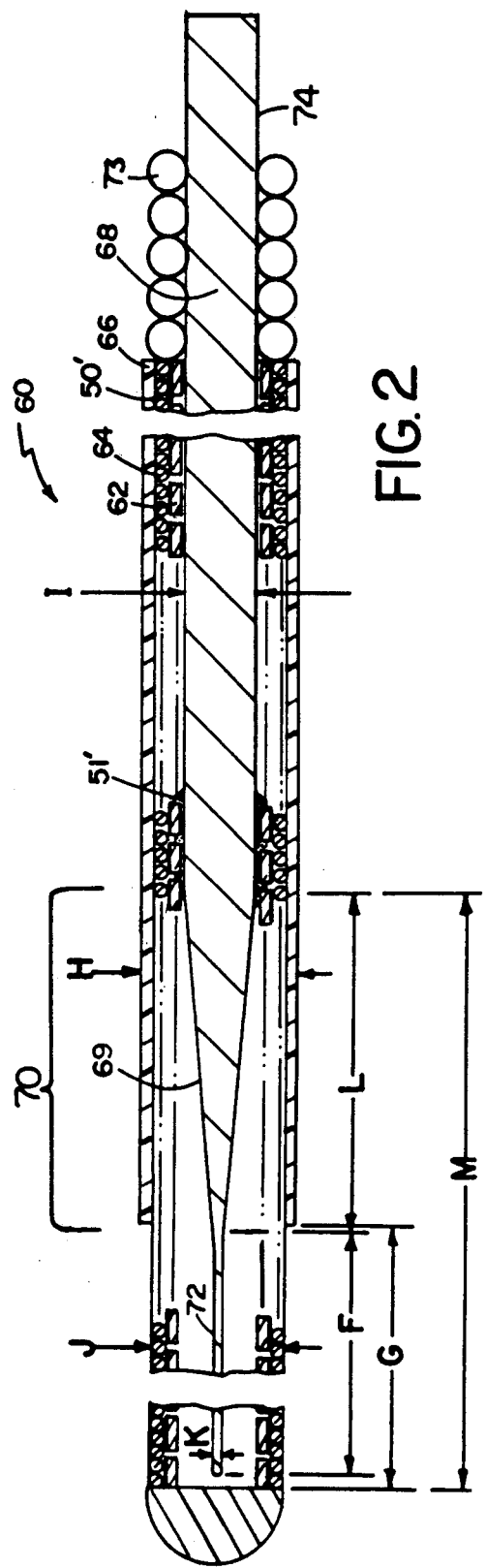

SMALL DIAMETER GUIDEWIRES OF MULTI-FILAR, CROSS-WOUND COILS

BACKGROUND OF THE INVENTION

This application is a continuation of application Ser. No. 07/276,106, filed Nov. 23, 1988, now abandoned, which was a continuation-in-part of U.S. patent application Ser. No. 170,514, filed Mar. 21, 1988, now U.S. Pat. No. 4,932,419, and entitled MULTI-FILAR, CROSS-WOUND COIL FOR MEDICAL DEVICES, the whole of which is hereby incorporated by reference herein.

This invention relates to medical guidewires, including medical injection wires.

Medical devices consisting of elongated spring coils are employed widely as guidewires, e.g., for negotiating narrow, tortuous passageways of the body to a site to be treated, and then serving as guides for catheters or other larger diameter devices advanced over the guidewires. In order to obtain maximum performance and patient safety, it is important that the guidewire be as small in diameter as possible, particularly in the tip region (but not so small as to create a danger of the tip breaking loose in the body); that the distal tip region be highly flexible to permit negotiation of difficult turns within the body; that the guidewire also be stiff enough axially to be advanced by pressure from the proximal end outside the body; and that the guidewire have good steerability or torque response, i.e., the tip-to-handle turn ratio should be as close to 1:1 as possible, without whipping. Most prior art guidewires offer a compromise of these desired features, e.g., trading tip flexibility for good torque response.

Another use of spring coils is in catheter-like medical injection wires or the like which require characteristics similar to those described above. An example of such a device is described in Tate, U.S. Pat. No. 3,841,308, as having a spring coil covered with a polyfluoroethylene flexible coating or sheath for delivery of fluid to ports adjacent the distal end.

SUMMARY OF THE INVENTION

This invention features guidewires, including injection wires, formed with a sheath and a multi-filar coil which cooperate to provide a guidewire having a small outer diameter while retaining a good torque from the proximal to the distal end. These guidewires are particularly suitable as injection wires when the sheath is formed of a material which forms a high tensile strength tube able to withstand high pressure in the range 300 to 900 p.s.i. Furthermore, as a result of its construction and consequent high pull strength, no safety wire is required to ensure that the tip of the quidewire remains integral with the rest of the guidewire.

In a first aspect, the invention features a medical guidewire having a distal tip portion for advancement through a body by application of force to a proximal end portion, including an elongated multi-filar coil structural element, and disposed thereabout and along the substantial portion of the length of the element a sheath, formed of material that is medically compatible and non-corrosive within the body, the sheath being adapted to flex in unison with the structural element without kinking, the sheath and structural element in combination having a torque response along the joined length approximating 1:1, thereby allowing control of the distal tip of the guidewire within a body by application of rotational force to the proximal end portion outside the body.

In related aspects, the guidewire has a core element formed of elongated metal disposed within the structural element; or the distal end of the structural element and the sheath are open to allow delivery of a fluid through the structural element to a body cavity.

In preferred embodiments, the material has a wall thickness of less than 0.0025 inch and also has the following characteristics: a) it is able to withstand a pressure of at least 300 psi, most preferably at least 700 psi, it has a tensile strength of at least 15,000 psi, it is not brittle, has a low elongation factor, and is dimensionally stable to allow radiopague fluid to be inserted into a body cavity through the guidewire in sufficient amount to provide good X-ray contrast at the site of insertion; b) it is resistant to heat at temperatures suitable for soldering, to allow soldering of material to the structural element; c) it has a uniform wall thickness so that it provides as little trauma to a body cavity as possible as it passes through the body; and d) it has no pin holes so that fluid does not leak through the material.

In other preferred embodiments, the sheath has a wall thickness of between 0.00075 and 0.0015 inch; the wall thickness varies by less than 0.0002 inch along the length of the sheath; and the inner diameter of the sheath is at least 0.0075 inch; the material is polyimide In yet other preferred embodiments, the core element has a distal tapered region and is fixedly attached within the structural element proximally from the tapered region; the structural element has an inner diameter greater than the outer diameter of the core element by about 0.0005 inch; the guidewire has an electron dense material in its distal region, most preferably the electron dense material is platinum; the guidewire further includes a sleeve positioned about the distal tapered region of the core element, the sleeve providing a transition between the core element and the tip of the guidewire thereby enhancing torque transmittal, most preferably the sleeve is formed of polyimide; the structural element is a cross-wound multi-filar element; the cross-wound multi-filar element includes an inner coil formed of wire having a flat cross-section; the sheath is fixed to the structural element, most preferably by bonding using cyanoacrylate; and the core element is soldered to the structural element.

In still other preferred embodiments, the sheath extends along the distal end of the structural element and is fixed at the distal end of the element; the distal end of the structural element and the sheath are open to allow delivery of a fluid to a body cavity; the structural element has an inner diameter of greater than 0.022 inch, and the guidewire has an outer diameter of less than 0.04 inch; and the distal end of the sheath is spaced from the distal tip of the structural element.

In a second aspect, the invention features a method for forming a guidewire including the steps of providing an elongated structural element and disposing thereabout along the majority of the length of the element a sheath formed of material resistant to heat at temperatures suitable for soldering, and glue bonding the material to the element.

Guidewires of this invention can be made to extremely small diameter (less than 0.018 inch) and provide high torque response (e.g., at least approaching 1:1) of proximal to distal ends with high visibility of the tip region. The polyimide sheath acts in conjunction with a wound multi-filar coil to provide this torque. The distal tip of the guidewire is without a sheath to provide a softer tip region. A core provided within a guidewire is fixed to the inner coil of the guidewire but is separated along the majority of its length from that coil by about 0.0005 inch. Thus, the core element only contacts the inner coil constantly when the guidewire is caused to bend, for example, around a curve in a body cavity. At these curves the contact with the core element provides better torque to the guidewire.

A polyimide sheath is particularly suited for use in this invention because it provides the features described above, and can be formed into an extremely thin walled material with small inner diameter. Injection wires of this invention provide means by which an extremely small diameter tube can be inserted within a body cavity and still allow a significant amount of fluid to be placed within the cavity at a desired site, since the injection wire has a relatively large lumen and can withstand high fluid pressure.

These and other features and advantages of the invention will be seen from the following description of the preferred embodiments thereof, and from the claims.

DESCRIPTION OF THE PREFERRED EMBODIMENTS

We first briefly describe the drawings.

Drawings

Figure 3:
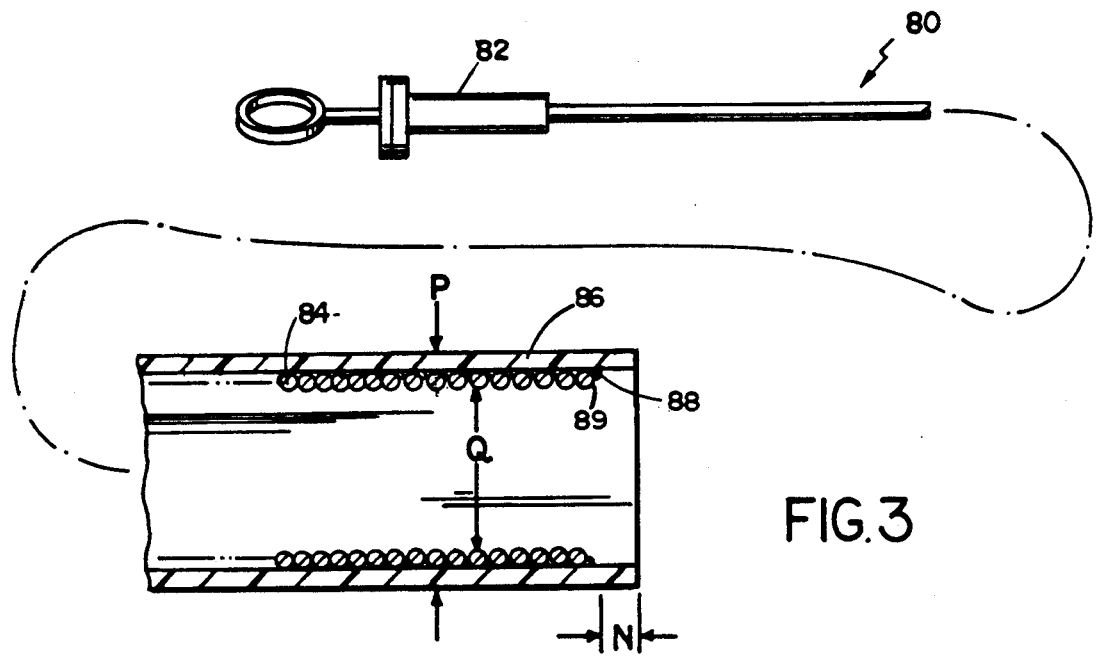
Figure 4:
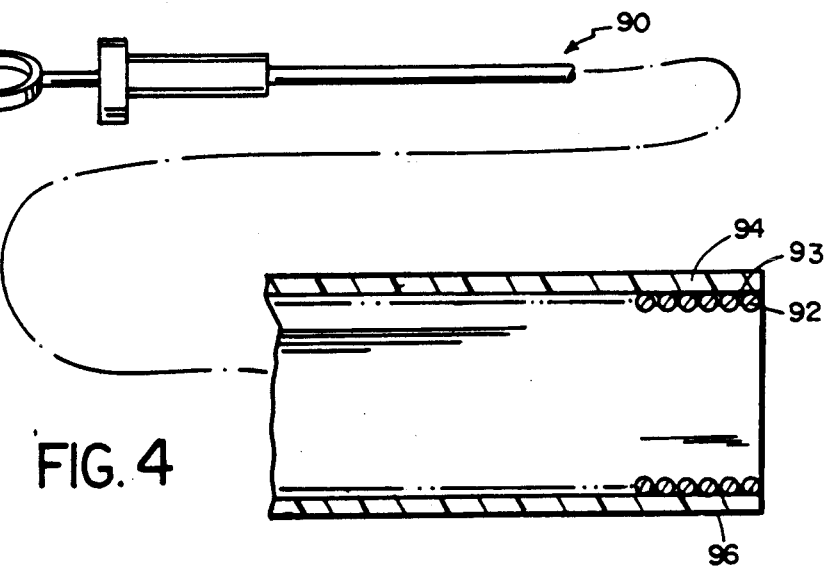

FIGS. 1 and 2 are sectional views of multi-filar cross-wound spring coil high torque guidewires of the invention; and FIGS. 3 and 4 are sectional views, partly in isometric view, of wound multi-filar guidewires formed as injection wires.

STRUCTURE

Referring to FIG. 1, torquable coronary guidewire 10 has a length of about 145 cm., an outer diameter A, about 0.018 inch, and is formed of an inner coil 12 and an outer coil 14 joined distally at a ball tip element 16, and joined proximally, e.g., by soldering, at a region 18. Inner coil 12 is bifilar, formed of two flat platinum wires, 20, 22, e.g., about 0.002 inch by 0.006 inch closely wound at a pitch ratio of about 2:1. Inner coil 12 extends only about 6-8 inches from ball tip element 16. Outer coil 14 is quadrifilar, formed of four stainless steel circular cross-sectional wires 24, 26, 28, 30 of between 0.002 and 0.003 inch diameter, which are closely wound about inner coil 12, but in a direction opposite to the winding direction of inner coil 12, with a pitch ratio of about 4:1. Outer coil 14 extends the length of guidewire 10.

A sheath 32 formed of polyimide (Hudson Wire Co., Trenton, Ga.) of thickness 0.00075 inch is provided tightly fitted around outer coil 14. Sheath 32 extends from proximal end 34 to a distance C, about 2-3 cm., from distal end 36. Distal end 38 of sheath 32 is fixed by glue 40 (e.g., cyanoacrylate) to outer coil 14, and along a length of about 3-4 cm. in the nearby distal region 33. Proximal end 39 of sheath 32 is bonded by cyanoacrylate 50 to the proximal end of outer coil 14.

Disposed within inner coil 12 is a core 42 formed of a stainless steel rod of outer base diameter B, about 0.010 inch, with about a 0.0005 inch clearance from inner coil 12. Core 42 and inner coil 12 interact by close fit interference. Core 42 has a distal tapered portion 44 of length about 6-8 inches corresponding generally to the length of inner coil 12, beginning at step 46. Core 42 is fixed to outer coil 14 proximally from tapered portion 44 by solder or adhesive 51.

Also provided is a polyimide sleeve 52 of length E, e.g., about 2 cm., outer diameter D, 0.0095 inch, and wall thickness 0.001 inch, slid onto the distal end of tapered portion 44 to provide a smooth transition from tapered portion 44 to ball tip element 16, and thereby increase torque transmission to ball tip element 16. Sleeve 52 is not fixed to ball tip element 16.

Referring to FIG. 2, there is shown another guidewire 60, of diameter H, about 0.018 inch, having a construction similar to guidewire 10, shown in FIG. 1 and described above. Guidewire 60 is formed with an inner coil 62 formed of a flat wire, and outer coil 64, formed of a circular wire, both extending the length of guidewire 60 and being encased within a polyimide sheath 66 along their length, except for a distance G of 3-5 cm. at the distal tip. Sheath 66 is bonded by cyanoacrylate (50') to outer coil 64 at its distal end, and inner coil 62 is soldered (51') at its proximal end to core 68, as described above. Inner core 68, of outer diameter I, about 0.006 inch, has a tapered tip 69 having a tapered region 70 of length L, about 3 cm., and a flat tip portion 72 of length F, about 2 cm. Proximal end 74 of core 68 has a single filar coil 73 attached to it (e.g., by adhesive) to provide a handle 74. As above, core 68 has a clearance from inner coil 62 of about 0.005 inch. Inner coil 62 and outer coil 64 are formed of stainless steel except for a distal region M, of length about 5 cm, formed of platinum and glued or soldered (not shown) to the stainless steel coils.

Referring to FIGS. 3 and 4 there are shown embodiments of a injection wire formed from a multi-filar coil having a polyimide sheath. A shown in FIG. 3, injection wire 80 has a length of about 100-150 cm., and is affixed at its proximal end to fluid delivery device 82, for example, a syringe. Injection wire 80 is formed of a bifilar or quadrifilar coil 84 of wire diameter 0.005 inch formed with a lumen of diameter Q, 0.027 inch, and enveloped by a polyimide sheath of nominal outer diameter P, 0.038 inch. Polyimide sheath 86 and coil 84 are fixed together at the extremities by glue 88 such that polyimide sheath 86 extends a distance N, about 0.5-2.0 millimeters, beyond a tip 89 of coil 84.

Referring to FIG. 4, injection wire 90 is formed as described above for injection wire 80, except coils 92 are fixed together by solder 93 to each other and subsequently bonded by cyanoacrylate to polyimide sleeve 94 in distal region 96 such that the tip of coil 92 and the tip of polyimide sheath 94 are adjacent and coextensive.

These injection wires are able to withstand high pressure fluid and allow delivery of substantial amounts of fluid to any desired region within a body cavity. These wires may be used in conjunction with a movable and removable core, or a standard 0.025 inch guidewire.

Other embodiments are within the following claims

I claim:

1. A medical guidewire having a distal tip portion for advancement through a body by application of axial force and by application of rotational force to a proximal end portion outside the body, said guidewire comprising:

an elongated cross-wound multi-filar coil structural element, said structural element comprising a first multi-filar coil segment and a second multi-filar coil segment, said first and second multi-filar coil segments disposed adjacent and in close proximity to one another along a portion of the length of said structural element, and a sheath formed of material that is non-corrosive within the body, said sheath disposed about and along a substantial portion of the length of said structural element, said sheath being adapted to flex in unison with said structural element without kinking, said sheath and the adjacent said first and second multi-filar coil segments of said elongated cross-wound multi-filar coil structural element relatively arranged and constructed, in combination, for interengagement in response to rotational force applied to the proximal end in a manner to provide a torque response, along the joined length, approaching 1:1, thereby allowing control of said distal tip of said guidewire within the body by application of rotational force to said proximal end portion outside the body.

2. A medical guidewire having a distal tip portion for advancement through a body by application of axial force and by application of rotational force to a proximal end portion outside the body, said guidewire comprising:

an elongated cross-wound multi-filar coil structural element, said structural element comprising a first multi-filar coil segment and a second multi-filar coil segment, said first and second multi-filar coil segments disposed adjacent and in close proximity to one another along a portion of the length of said structural element, and a sheath formed of material that is non-corrosive within the body, said sheath disposed about and along a substantial portion of the length of said structural element, said sheath being adapted to flex in unison with said structural element without kinking, said sheath and the adjacent said first and second multi-filar coil segments of said elongated cross-wound multi-filar coil structural element relatively arranged and constructed, in combination, for interengagement in response to rotational force applied to the proximal end in a manner to provide a torque response, along the joined length, approaching 1:1, thereby allowing control of said distal tip of said guidewire within the body by application of rotational force to said proximal end portion outside the body; the distal end of said elongated cross-wound multi-filar coil structural and said sheath defining an opening for delivery of a fluid through said element to a body cavity.

3. The guidewire of any one of claims 1 or 2 wherein said sheath is disposed along the majority of said element, and has a wall thickness of less than 0.0025 inch.

4. The guidewire of any one of claims 1 or 2, wherein said material is able to withstand a pressure of at least 300 psi.

5. The guidewire of claim 4, wherein said material is able to withstand a pressure of at least 700 psi; whereby said material can allow radiopaque fluid to be inserted into a body cavity through said guidewire in sufficient amount to provide good X-ray contrast at the site of insertion, 6. The guidewire of any one of claims 1 or 2, wherein said material has a tensile strength of at least 15,000 psi, is not brittle, has a low elongation factor and is dimensionally stable; whereby said material can allow radiopaque fluid to be inserted into a body cavity through said guidewire in sufficient amount to provide good X-ray contrast at the site of insertion.

7. The guidewire of any one of claims 1 or 2 wherein said material is resistant to heat at temperatures suitable for soldering, to allow soldering of material to said structural element.

8. The guidewire of any one of claims 1 or 2 wherein said material has a uniform wall thickness so that said guidewire provides as little trauma to said body cavity as possible as it passes through said body cavity.

9. The guidewire of any one of claims 1 or 2 wherein said material is impermeable to leakage of fluid through said material.

10. The guidewire of any one of claims 1 or 2 said sheath having a wall thickness of between 0.00075 and 0.0015 inch.

11. The guidewire of any one of claims 1 or 2 said wall thickness varying less than 0.0002 inch along the length of said sheath.

12. The guidewire of any one of claims 1 or 2 said sheath having an inner diameter of at least 0.0075 inch.

13. The guidewire of any one of claims 1 or 2 said material being polyimide.

14. The guidewire of any one of claims 1 or 2 wherein said sheath is fixed to said structural element.

15. The guidewire of claim 14, wherein said sheath is fixed by glue to said structural element.

16. The guidewire of claim 2 said structural element having an inner diameter of greater than 0.022 inch and said guidewire being an outer diameter of less than 0.040 inch.

17. A medical guidewire having a distal tip portion for advancement through a body by application of axial force and by application of rotational force to a proximal end portion outside the body, said guidewire comprising:

an elongated cross-wound multi-filar coil structural element, said structural element comprising a first multi-filar coil segment and a second multi-filar coil segment, said first and second multi-filar coil segments disposed adjacent and in close proximity to one another along a portion of the length of said structural element, and a sheath formed of material that is non-corrosive within the body, said sheath disposed about and along a substantial portion of the length of said structural element, said sheath extending along the distal end of said structural element and being fixed at the distal end of said element, and said sheath being adapted to flex in unison with said structural element without kinking, said sheath and the adjacent said first and second multi-filar coil segments of said cross-wound multi-filar coil structural element relatively arranged and constructed, in combination, for interengagement in response to rotational force applied to the proximal end in a manner to provide a torque response, along the joined length, approaching 1:1, thereby allowing control of said distal tip of said guidewire within the body by application of rotational force to said proximal end portion outside the body.

18. The medical guidewire of claim 17 wherein the distal end of said multi-filar coil structural element and said sheath being open to allow delivery of a fluid through said element to a body cavity.

19. The guidewire of claims 17 or 18 wherein said structural element comprises a cross wound multi-filar element.

20. The guidewire of claims 17 or 18, the distal end of said sheath being spaced from the distal end of said structural element.

* * * * *

UNITED STATES PATENT AND TRADEMARK OFFICE
CERTIFICATE OF CORRECTION

PATENT NO.   : 5,065,769
DATED        : NOVEMBER 19, 1991
INVENTOR(S)  : FERNANDO A. DE TOLEDO

It is certified that error appears in the above-identified patent and that said Letters Patent is hereby corrected as shown below:

Col. 2, line 14, change "radiopague" to --radiopaque--
         line 27; after "polyimide" insert --.--;

Col. 4, line 27; change "0.005" to --0.0005--;
         line 57; after "claims" insert --.--.

Signed and Sealed this

Twentieth Day of April, 1993

Attest:

MICHAEL K. KIRK

*Attesting Officer*      *Acting Commissioner of Patents and Trademarks*